United States Patent [19]

Russell

[11] Patent Number: 5,628,772

[45] Date of Patent: May 13, 1997

[54] THERAPEUTIC MASSAGE MASK

[75] Inventor: Robin Russell, Scottsdale, Ariz.

[73] Assignee: R-Jayco Ltd., Inc., Scottsdale, Ariz.

[21] Appl. No.: 572,534

[22] Filed: Dec. 14, 1995

[51] Int. Cl.$^6$ ................................................. A61F 7/00
[52] U.S. Cl. ................... 607/109; 607/112; 601/112; 601/113; 601/115; 601/131; 601/37
[58] Field of Search ........................ 607/109–112; 601/115–148

[56] References Cited

U.S. PATENT DOCUMENTS

| | | |
|---|---|---|
| 702,759 | 6/1902 | Allegretti . |
| 2,755,803 | 7/1956 | Dorsey . |
| 2,796,903 | 6/1957 | Gazelle ................................ 607/109 |
| 3,491,761 | 1/1970 | Baker . |
| 4,372,318 | 2/1983 | Viesturs . |
| 4,614,189 | 9/1986 | MacKenzie . |
| 4,761,314 | 8/1988 | Marshall ................................ 428/11 |
| 5,119,812 | 6/1992 | Angelo . |
| 5,274,865 | 1/1994 | Takehashi . |
| 5,344,437 | 9/1994 | Pistay . |

*Primary Examiner*—Sam Rimell
*Assistant Examiner*—Robert V. Racunas
*Attorney, Agent, or Firm*—LaValle D. Ptak

[57] ABSTRACT

A therapeutic massage mask comprises an elongated resilient plastic pouch having a length and width which is greater than the thickness thereof. The pouch is filled with a plurality of spherical balls made of a thermal transfer material, such as hard plastic, ceramic, or hollow spheres filled with BLUE ICE® material. The pouch is placed in a freezer to lower the temperature of the balls located within it. Subsequently, the pouch then may be applied to overlie a portion of the human body and a gentle rolling action on the side of the pouch opposite the body causes the balls to transfer a massaging action to the portion of the body underlying the pouch. At the same time, the balls function to cool the underlying body portion, thereby serving a dual function.

12 Claims, 1 Drawing Sheet

THERAPEUTIC MASSAGE MASK

BACKGROUND

Persons suffering from migraine headaches and patients recovering from surgery, or who are being treated for sports injuries and the like, frequently find it desirable to apply thermal treatment to the affected area. Thermal treatment, such as heat or cold, is employed to reduce swelling, relieve pain and otherwise soothe the area undergoing treatment.

A common practice in applying thermal treatment to a patient's face, particularly in the region of the eyes, has been to employ an icebag, which typically is filled with a mixture of crushed ice and water. Icebags, however, do not conform well to the contours of a person's face; and they are difficult to hold in place. An early effort at tailoring or shaping such a bag over the eye region of a person is found in the Allegretti U.S. Pat. No. 702,759. The bag of Allegretti is specifically shaped to conform generally to the forehead and eyes of a person, and includes a strap to hold it against the face while it is use. Heat transfer between the area of the body (namely, the eye region) against which the bag is placed and the fluid within the bag then takes place through the bag itself. A more recent patent to a similar type of shaped water bag is disclosed in the MacKenzie U.S. Pat. No. 4,614,189.

Water bags or ice bags, whether they are general purpose bags or specifically shaped to conform to the face, as in the case of the bags of Allegretti and MacKenzie, have a distinct disadvantage in use. The ice/water solution rapidly attains the temperature of the underlying area being treated; and furthermore it is necessary, once the cooling effect has been depleted, to empty the bag and refill it with a new ice/water mixture for continued use. This is a messy and time consuming procedure.

Thermal treatment devices specifically directed to the treatment of the facial region in the location of the eyes, which have been developed to overcome some of the disadvantages of the ice bag configurations of MacKenzie and Allegretti, are disclosed in the Viesturs U.S. Pat. No. 4,372,318 and Gazelle U.S. Pat. No. 2,796,903. The devices of both of these patents have a pair of compartments which are shaped to overlie a person's face in the region of the eyes. The compartments of the devices disclosed in both of these patents are provided with relatively wide openings to facilitate the insertion of ice into the compartments. The devices then are self sealing; and straps are provided to hold them on the face, against the eyes, in order to effect the thermal treatment. Although the use of the bags of Gazelle and Viesturs is facilitated by nature of the access openings to the ice compartments, it still is necessary to empty the compartments and refill them with ice or a mixture of ice and water each time the cooling effect of the ice has been depleted. The coolant located within the bags is discarded, once thermal equilibrium is reached.

The Dorsey U.S. Pat. No. 2,755,803 is a somewhat different approach, which employs an eye shield with a compartment for holding a sponge. The sponge is immersed in either hot or cold water, placed in the compartment, and then the shield is placed against the eyes and is held there by a strap which goes around the head. The device of this patent, however, is a somewhat less effective thermal transfer device than the ones of the patents described above, since no ice is employed but merely a water filled sponge. Replacement of the sponge, however, can be effected relatively quickly and easily during the course of treatment.

The Angelo U.S. Pat. No. 5,119,812 and Takehashi U.S. Pat. No. 5,274,865 are directed to ice masks or cooling devices which do not require emptying and refilling of the reservoir during use. The device of Angelo includes a sealed mask with a number of individual compartments formed in it. The compartments are each filled with a thermal storage material in the form of a gelatinous substance of the type used for artificial ice cubes, sold under a variety of different trade names, such as BLUE ICE®. Thus, the mask may be placed in a freezer to cool down the sections; and because the sections are separated, the mask may be conformed to the face of the user to effect thermal transfer between the face region behind the mask and the thermal storage material in the various compartments.

The Takehashi patent is a cooling pillow which is filled with a mixture of fine particles of hard carbon and water. The device is cooled and then applied against a portion of the head of a user to effect the thermal transfer. As with the device of Angelo, upon attainment of thermal equilibrium, the Takehashi device once again may be placed in a freezer or other suitable cooling environment to reduce the temperature of the material with which it is filled. No emptying and refilling of the devices of either Takehashi or Angelo is necessary to permit their reuse.

While all of the thermal treatment devices or ice masks which have been described above are capable of effecting a thermal transfer between the cooling material contained within the device and the portion of the body against which it is placed, none of them are capable of utilization for massaging the affected region behind the mask. An attempt to provide both a thermal transfer material and a massage effect simultaneously is disclosed in the Pistay U.S. Pat. No. 5,344,437. This patent discloses a pillow in a U-shaped form. Extensions fit around the neck, with a thicker upper portion in intimate contact with the posterior portion of the head of a person using the pillow. On each side of the pillow, a pocket is provided which may be filled with a thermal transfer material, such as packets of gelatinous artificial ice material which may be frozen and reused to effect a thermal transfer. An electric vibrator also is embedded in a foam housing within the pillow. When the vibrator is turned on, the entire pillow operates as a vibrator massage; and the separate thermal transfer packets in the pockets effect the heat transfer desired. It is to be noted, however, that the thermal transfer packets and the vibrator operate independently of one another; although both of them are incorporated into the pillow.

It is desirable to provide a therapeutic mask which is particularly suitable for operation in the region of the eyes of a person, which overcomes the disadvantages of the prior art, and which is capable of providing both a thermal treatment and a massage treatment, simultaneously, to the area underlying the mask.

SUMMARY OF THE INVENTION

It is an object of this invention to provide an improved therapeutic device.

It is another object of this invention to provide an improved therapeutic thermal transfer device.

It is an additional object of this invention to provide an improved therapeutic massage mask.

It is a further object of this invention to provide an improved combined massage and thermal treatment device.

In accordance with a preferred embodiment of the invention, a therapeutic massage mask includes a flexible hollow pouch which is shaped to overlie a portion of a human body. The pouch is filled with a plurality of individual spherically-shaped balls made of a material for effecting thermal transfer. A massage effect is obtained by applying moving pressure through the pouch to the balls when the pouch overlies the body portion to be treated, simultaneously effecting both a thermal treatment and a massage treatment to the affected area.

DETAILED DESCRIPTION

Figure 1:
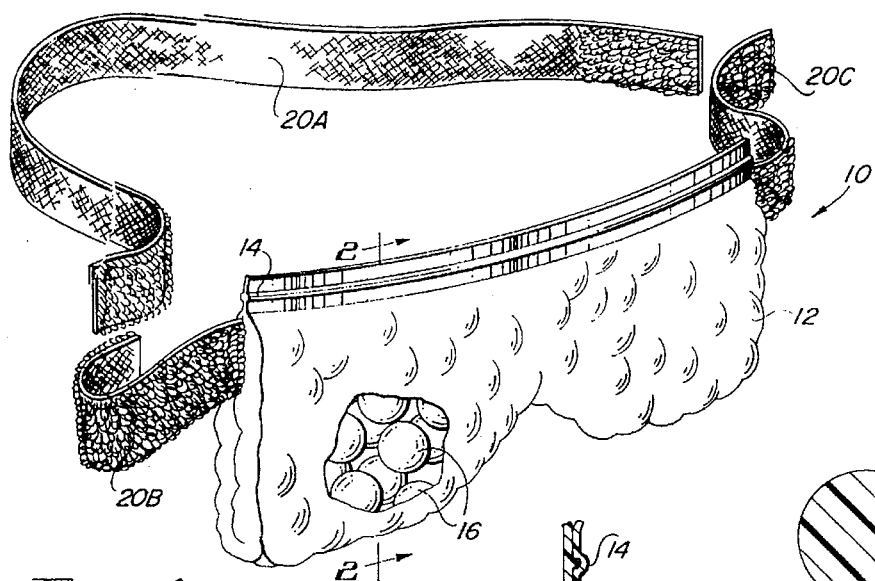
FIG. 1 is a front perspective, partially cut away view of a preferred embodiment of the invention.

Reference now should be made to the drawings, in which the same reference numbers are used throughout the different figures to designate the same components. FIG. 1 is a front perspective view of a therapeutic massage mask 10 constructed in accordance with a preferred embodiment of the invention. As illustrated, the mask 10 is configured to fit over the eyes, the lower forehead and upper cheeks of a user to provide therapeutic cooling and massage to the region of the face of the user (the eye region) located directly behind the mask 10.

Figure 2:
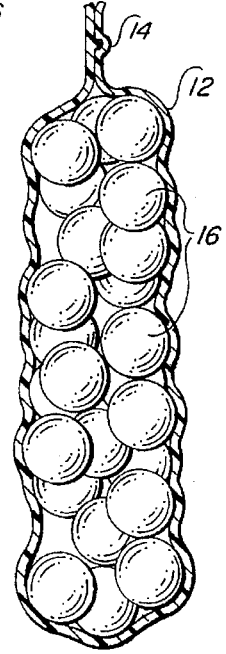
FIG. 2 is a cross-sectional view taken along the line 2—2 of FIG. 1.
Figure 5:
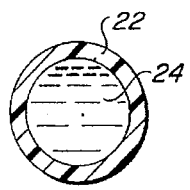
FIG. 5 illustrates an alternative to the portion shown in FIG. 4.

The mask 10 comprises a flexible hollow pouch 12, preferably made of resilient hollow plastic or rubber-like material having relatively thin, strong walls. The pouch 12 has a hollow interior thickness which is less than its overall length and height, as illustrated most clearly in FIGS. 2 and 3. In construction, the pouch 12 is open along its upper edge. As shown in FIGS. 1 and 2, this edge may be closed with a resealable fastener 14 of the type commonly used for plastic food storage bags.

Figure 4:
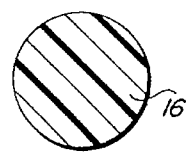
FIG. 4 illustrates a cross-sectional detail of a portion of the embodiment shown in FIGS. 1, 2 and 3.

The interior of the pouch 10 is filled with a number of spherical plastic balls 16, typically having a diameter in the range of ⅛" to ⅜". The balls 16 are made of thermal transfer material designed to effect a prolonged cooling effect to the facial region of the person wearing the mask 10 by means of thermal transfer between the balls 16 and the face of the user. Typically, the entire mask 10 is placed in a freezer to cool the balls 16 down to a low temperature, substantially below freezing. To provide the desired thermal transfer, the balls 16 preferably are made of a ceramic material 16, as shown in FIG. 4, or may be hollow plastic spheres 22 filled with a slurry or insoluble hydrophilic gel which can be frozen. This material is sold under various trademarks, including "BLUE ICE". Other materials are available for the gel 24 in the sphere 22. Whatever material the spherical balls 16 or 22 are made of, the desirable characteristic is the ability to cool the materials to a very low temperature (in the vicinity of 0° Fahrenheit) while maintaining their shape during thermal transfer to temperatures up to and including human body temperature and room ambient temperatures. The spherical balls 16 or 22 also should be capable of retaining their generally spherical shape while undergoing mild pressure, as described subsequently.

Figure 3:
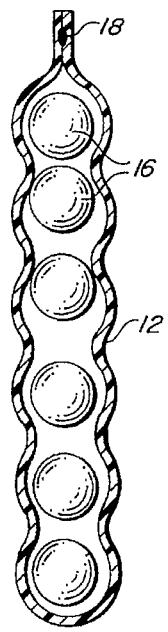
FIG. 3 is an alternative to the cross-sectional configuration shown in FIG. 3.

When the configuration shown in FIGS. 1 and 2 is used, balls 16 or 22 may be added to or removed from the pouch 12, as desired, to obtain the maximum therapeutic effect from the massage mask. An alternative construction is shown in FIG. 3 where the thickness of the pouch 12 is only slightly greater than the diameter of the balls 16. Thus, a single layer of balls 16 or 22 is loosely held within the confines of the pouch 12. As illustrated in FIG. 3, the upper edge of the pouch 12 also may be permanently sealed with an ultrasonic weld 18 or a chemical closure to prevent subsequent removal of the balls 16 from the pouch 12. Whether the configuration of FIGS. 1 and 2 or that of the alternative configuration of FIG. 3 is used, however, the overall operation and function of the masks 10 of the different embodiments is the same.

To facilitate placement of the mask over the upper facial area (the eye area) and to hold it in place, an adjustable strap 20A, having one-half of a hook-and-loop fastener located on each of its ends is attached to a pair of extensions 20B and 20C secured to opposite sides of the pouch 12, as illustrated in FIG. 1. The extensions 20B and 20C each comprise the other half of a hook-and-loop fastener; so that adjustment to various head sizes may be effected by means of the placement of the ends of the strap 20A on the mating fastener portions 20B and 20C. Of course other types of fasteners, including snaps, buttons, buckles and the like, may be used to hold the strap 20A securely but comfortably around the head of the user. This permits the pouch 12 to be worn much in the same manner as a pair of eyeglasses; so that it will remain in place even if the person using it is in an upright position.

When the pouch 12 is removed from the freezer or other cooling environment used to lower the temperature of the heat transfer balls or spheres 16 or 22, it is placed over the face of the user, as described. Once the pouch 12 is in place, the user then also may apply a gentle rolling pressure action on the outer surface of the pouch (facing toward the right as shown in FIG. 1), to press it gently against the eye region to cause a rolling massage effect to take place by means of the slight movement of the spherical balls 16 or 22 against the opposite side (the face side) of the wall of the pouch 12 and onto the eye region located behind the pouch 12. Thus, the mask 10 provides a dual purpose, namely that of a thermal transfer to cool the eye region, and, simultaneously, a massaging of the region located behind the mask. Since the balls 16 or 22 are each separate, individual balls, not interconnected to one another, their rolling relative movement effects this desired massage when a gentle moving pressure is applied to them through the opposite outer surface of the pouch 12.

Once thermal equilibrium has been reached between the balls 16 or 22 located inside the pouch 12 and the area of the body to which the massage mask 12 is applied, the mask 12 may be removed and replaced with another one which has ben cooled. The original mask then may be placed back into the freezer or other cooling device to lower the temperature of the balls 16 or 22 located within it for subsequent use. Consequently, the mask is reusable without requiring it to be emptied and refilled of any heat transfer materials. Since no liquids are placed within the mask, it readily may be conformed to the underlying region of the face upon application, because of the spherical balls 16 or 22 are independent of one another.

Figure 6:
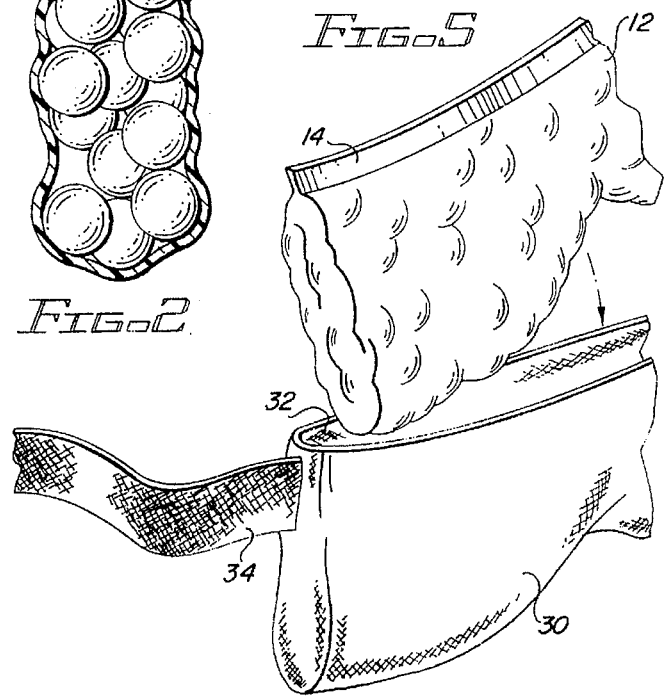
FIG. 6 illustrates a variation of the embodiment shown in FIG. 1 in a different manner of use.

FIG. 6 is directed to a variation of the embodiment shown in FIG. 1, where the pouch 12 of FIG. 1 does not include any strap attachments such as 20B and 20C on it. The pouch 12 shown in FIG. 6 is identical in all other respects to the pouch shown in FIGS. 1 and 2. An additional holding member 30 made of a soft, soothing, washable material such as cotton or the like may be used with a strap arrangement attached to it similar to the one 20A, 20B and 20C, or, as illustrated in FIG. 6, an elastic band 34 is connected to opposite sides of the member 30 in the same manner as the straps 20B and 20C are connected to the pouch 12 of FIG. 1. The elastic band 34, however, is permanently attached to the open pouch 30, which has an opening 32 in its top to permit insertion of the therapeutic massage mask pouch 12 into it.

One of the advantages of the configuration shown in FIG. 6 is that the cloth material of the holding member 30 serves to buffer the instant thermal shock which may otherwise occur from placing the pouch 12 directly from the freezer onto the face of a user. The thermal transfer which is effected through the walls of the pouch holding member 30 is not as direct; and a slight delay in the attainment of an equilibrium temperature between the temperature of the frozen spherical balls 16 or 22 and the face of the user through the cloth of the member 30 is obtained.

In all other respects, however, the operation of the device of FIG. 6 is the same as described above in conjunction with the pouch 12 alone, as shown in FIG. 1. The massaging action takes place through the outer wall of the pouch holding member 30, as well as the wall of the pouch 12; but since the thicknesses of these walls is insignificant, a very soothing rolling massage is effected by a light pressure movement on the balls 16 or 22 located within the pouch 12 when the mask is pressed against the face of the user.

A second advantage to the utilization of the pouch holding member 30 of FIG. 6 is that the pouches 12 are readily inserted and removed from the pouch holding member 30 through its open upper end 32. Consequently, when the desired cooling effect of the spherical balls 16 or 22 within the pouch 12 no longer takes place, due to the warming up of the balls 16 or 22, an original pouch 12 may be removed and placed in the freezer and immediately replaced with another similar pouch 12 which has attained its desired cold temperature. Thus, by rotating two or more pouches 12 into the pouch holding member 30, a constant cooling effect may be achieved. The member 30 also may be made of washable material; so that it readily can be cleaned between uses.

The foregoing description of the preferred embodiment of the invention is to be considered as illustrative and not as limiting. For example, the device may be applied to areas other than the face. Various changes and modifications will occur to those skilled in the art for performing substantially the same function, in substantially the same way, to achieve substantially the same result, without departing from the true scope of the invention as defined in the appended claims.

What is claimed is:

1. A therapeutic massage mask including in combination:

a flexible hollow pouch shaped to overlie a portion of a human body; and a plurality of individual, generally spherically-shaped balls made of thermal transfer material, which remains solid at ambient room temperature carried inside said pouch to permit a massage effect to be obtained by applying moving pressure through said pouch to said balls; said balls retaining said substantially spherical shape at room temperature and having a diameter substantially in the range of 1/8" to 3/8".

2. The combination according to claim 1 wherein said flexible hollow pouch is made of resilient plastic.

3. The combination according to claim 2 wherein said flexible hollow pouch is an elongated pouch having a length and width substantially greater than the thickness thereof.

4. The combination according to claim 3 further including a releasable securing device for securing said pouch to a portion of a human body.

5. The combination according to claim 4 wherein said securing device includes a hollow holding member dimensioned to receive said flexible hollow pouch.

6. The combination according to claim 5 wherein said hollow holding member includes an elongated strap for releasably holding said holding member with said flexible hollow pouch therein against a portion of a human body.

7. The combination according to claim 4 wherein said securing device includes an elastic strap.

8. The combination according to claim 4 wherein said securing device includes a strap and a releasable fastener attached to said hollow pouch.

9. The combination according to claim 4 wherein said pouch has a sealable opening therein to permit the insertion and removal of said balls.

10. The combination according to claim 1 further including a releasable securing device for securing said pouch to a portion of a human body.

11. The combination according to claim 10 wherein said securing device includes a hollow holding member dimensioned to receive said flexible hollow pouch.

12. The combination according to claim 11 wherein said hollow holding member includes an elongated strap for releasably holding said holding member with said flexible hollow pouch therein against a portion of a human body.

* * * * *